United States Patent [19]

Raduechel et al.

[11] Patent Number: 5,047,525
[45] Date of Patent: Sep. 10, 1991

[54] 9-HALOPROSTAGLANDIN CLATHRATES AND THEIR USE AS MEDICINES

[75] Inventors: Bernd Raduechel; Werner Skuballa; Olaf Loge; Johann-Wilhelm Tack, all of Berlin, Fed. Rep. of Germany

[73] Assignee: Schering Aktiengesellschaft, Berlin and Bergkamen, Fed. Rep. of Germany

[21] Appl. No.: 549,045

[22] Filed: Jul. 6, 1990

Related U.S. Application Data

[63] Continuation of Ser. No. 349,374, May 8, 1989, abandoned, which is a continuation of Ser. No. 205,966, Jun. 13, 1988, abandoned, which is a continuation of Ser. No. 931,590, filed as PCT DE 86/00039 on Feb. 4, 1986, abandoned.

[30] Foreign Application Priority Data

Feb. 4, 1985 [DE] Fed. Rep. of Germany ....... 3504044

[51] Int. Cl.⁵ ...................... C08B 37/16; A01N 43/04
[52] U.S. Cl. ...................................... 536/103; 560/119
[58] Field of Search .................... 536/103, 46; 514/58, 514/691, 729; 560/119

[56] References Cited

U.S. PATENT DOCUMENTS

| | | | |
|---|---|---|---|
| 3,816,393 | 6/1974 | Hayashi et al. | 536/103 |
| 4,444,788 | 4/1984 | Skuballa et al. | 514/445 |
| 4,454,339 | 6/1984 | Skuballa et al. | 560/55 |

Primary Examiner—Nathan M. Nutter
Attorney, Agent, or Firm—Millen, White & Zelano

[57] ABSTRACT

The present application encompasses pharmaceutical preparations, characterized in that they contain as the active component a cyclodextrin clathrate of a prostaglandin of general Formula I

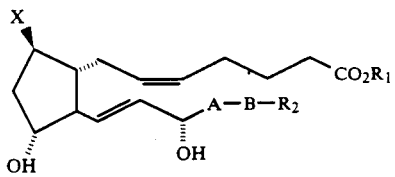

wherein
$R_1$ is a hydrogen atom or a straight-chain or branched alkyl residue of up to 10 carbon atoms,
$R_2$ is an alkyl, cycloalkyl, or optionally substituted phenyl group,
A and B jointly mean a direct bond or
A means a straight- or branched-chain alkylene group of up to 10 carbon atoms and
B means an oxygen atom, a direct bond, or a —C≡C—bond, and
X means a chlorine or fluorine atom.

9 Claims, No Drawings

9-HALOPROSTAGLANDIN CLATHRATES AND THEIR USE AS MEDICINES

This is a continuation of application Ser. No. 07/349,374, filed May 8, 1989, now abandoned, which is a continuation of application Ser. No. 07/205,966, filed June 13, 1988, now abandoned, which is a continuation of application Ser. No. 06/931,590, filed as PCT DE86/00039 on Feb. 4, 1986, now abandoned.

The present invention relates to cyclodextrin clathrates of 9-haloprostaglandin analogs, and to agents containing same.

9-Chloro- or 9-fluoroprostaglandin analogs are pharmacologically and medicinally valuable active agents, the preparation and utilization of which have been described in DOS 2,950,027 and 3,126,924. These compounds, as compared with the corresponding natural prostaglandins, possess, with a similar spectrum of activity, a substantially improved specificity and, above all, a substantially longer-lasting effect.

Frequently, the 9-chloro- and, respectively, 9-fluoroprostaglandins disclosed in the above-mentioned laid-open applications are present in a noncrystalline form; as a consequence, their pharmaceutical usage is limited. Additionally, they exhibit limited water solubility and dissolution rate.

It has now been discovered that clathrate compounds of these 9-chloro- and 9-fluoroprostaglandins with cyclodextrins do not show the aforementioned disadvantages, i.e. their water-solubility is improved, the dissolution rate is increased, and the clathrate compounds are present in crystalline form. Besides, their stability, for example with respect to heat, light, and oxygen is enhanced, and their galenic preparation (production of solutions or tablets) is facilitated.

The invention relates to cyclodextrin clathrates of prostaglandins of general Formula I

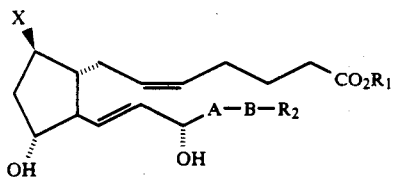

wherein
$R_1$ is a hydrogen atom or a straight-chain or branched alkyl residue of up to 10 carbon atoms,
$R_2$ is an alkyl, cycloalkyl, or optionally substituted phenyl group,
A and B jointly mean a direct bond or
A means a straight- or branched-chain alkylene group of up to 10 carbon atoms and
B means an oxygen atom, a direct bond, or a —C≡C—bond, and
X means a chlorine or fluorine atom.

Straight- or branched-chain alkyl groups $R_1$ are intended to mean, for example, methyl, ethyl, propyl, isopropyl, butyl, isobutyl, sec-butyl, tert-butyl, pentyl, hexyl, decyl.

Suitable alkyl groups $R_2$ are straight- and branched-chain, saturated and unsaturated alkyl residues, preferably saturated ones, of up to 10 carbon atoms. Examples that can be cited are methyl, ethyl, propyl, butyl, isobutyl, pentyl, isobutenyl, octyl, or 1,1-dimethylpentyl.

The cycloalkyl group $R_2$ can contain in the ring 3–10, preferably 5 or 6 carbon atoms. Examples are cyclopropyl, cyclobutyl, cyclopentyl, cyclohexyl.

The phenyl group $R_2$ can optionally be substituted by halogen, $C_{1-4}$-alkoxy, $C_{1-4}$-alkyl, trifluoromethyl or halogen-substituted $C_{1-4}$-alkyl.

Suitable as the alkylene group A are straight-chain or branched, saturated and unsaturated alkylene residues, preferably saturated ones of up to 10 carbon atoms. Examples that can be mentioned are methylene, ethylene, dimethylmethylene, ethylethylene, trimethylene, tetramethylene.

$R_2$, A and B can be selected so that the 16-position is substituted by one or two alkyl groups, for example methyl or ethyl, preferably methyl.

In order to prepare the clathrate compounds of this invention, the compounds of general Formula I are dissolved in a pharmacologically acceptable alcohol, preferably ethanol, and added at 60° C. to aqueous solutions of α-, β- or γ-cyclodextrin, preferably β-cyclodextrin. After cooling, the corresponding clathrates are crystallized and can be isolated as solid, free-flowing crystals by suctioning and drying.

The clathrate compounds produced in accordance with this invention are valuable pharmaceuticals. They exhibit strong inhibiting activity on gastric acid secretion and protect the mucosa of the stomach against various deleterious influences, such as, for example, ethanol, hydrochloric acid, hot water, and stress, as well as against anti-inflammatory substances, such as aspirin or indomethacin.

Several of the clathrates according to this invention are excellently suited for the treatment of allergic and vasomotor rhinitis since they bring about a rapid reduction in the swelling of the nasal mucosa.

Several of the clathrates of this invention are furthermore suitable, upon enteral or parenteral administration, for inducing menstruation or interrupting pregnancy.

They are also suitable for synchronizing the sexual cycle of female mammals, such as rabbits, cattle, horses, and pigs. Furthermore, they are suitable for cervix dilation as a preparation for diagnostic or therapeutic interventions.

The clathrates of the invention can be utilized in liquid or solid galenic formulations, and the formulations can be administered enterally, parenterally, vaginally or rectally.

For the production of tablets, the prostaglandincyclodextrin clathrate is mixed with excipients and auxiliary agents, such as lactose, cornstarch, polyvinylpyrrolidone and magnesium stearate.

For the preparation of solutions for enteral and parenteral use, the aqueous cyclodextrin solutions are lyophilized together with lactose. Subsequently the lyophilized products can be brought to the desired concentration with physiological sodium chloride solution.

Consequently, the invention encompasses pharmaceutical preparations and formulations containing as the active ingredient a cyclodextrin clathrate of a 9-chloro- or 9-fluoroprostaglandin analog.

The invention will be described by the examples set forth below:

EXAMPLE 1

At 80° C., 4.90 g of β-cyclodextrin is dissolved in 35 ml of water, cooled to 60° C., and a solution of 175 mg of (5Z,13E)-(9R,11R,15R)-9-chloro-11,15-dihydroxy- 16,16-dimethyl-5,13-prostadienoic acid in 2.6 ml of ethanol is added dropwise within 15 minutes. The mixture is agitated for another 1.5 hours at 60° C. and then allowed to cool down overnight under agitation. The thus-precipitated solid is suctioned off, washed with 25 ml of a mixture of water-ethanol (1:1), and dried for 6 hours at 40° C. and 0.1 torr over phosphorus pentoxide, thus obtaining 2.88 g of freely flowing crystals of β-cyclodextrin clathrate compound of the above-mentioned 9-chloroprostaglandin analog.

The content of 9-chloroprostaglandin analog in the clathrate was determined by high pressure liquid chromatography and was 5.2%.

EXAMPLE 2

At 60° C., a solution of 42 mg of (5Z,13E)-(9R,11R,15R)-9-fluoro-11,15-dihydroxy-16-phenoxy-17,18,19,20-tetranor-5,13-prostadienoic acid in 0.6 ml of ethanol is added dropwise to a solution of 1.225 g of β-cyclodextrin in 8.75 ml of water; the mixture is stirred for 2 hours at 60° C. and then is allowed to cool down. After 24 hours, the crystals are suctioned off, washed with 6 ml of water ethanol (1:1), and dried at 40° C. at 0.1 torr over phosphorus pentoxide for 6 hours, yielding 0.68 g of freely flowing crystals of the β-cyclodextrin clathrate of the above-mentioned 9-fluoroprostaglandin analog.

The content of 9-fluoroprostaglandin analog in the clathrate was determined by high pressure liquid chromatography and amounted to 5.1%.

By following the procedure described in Examples 1 and 2, the β-cyclodextrin clathrate compounds of the following analogs can be produced:

(5Z,13E)-(9R,11R,15R)-9-chloro-11,15-dihydroxy-16-phenoxy-17,18,19,20-tetranor-5,13-prostadienoic acid
(5Z,13E)-(9R,11R,15R)-9-fluoro-11,15-dihydroxy-16,16-dimethyl-5,13-prostadienoic acid
(5Z,13E)-(9R,11R,15R)-9-chloro-11,15-dihydroxy-16,16,20-trimethyl-18,18,19,19-tetradehydro-5,13-prostadienoic acid.

EXAMPLE 3

The β-cyclodextrin clathrate of (5Z,13E)-(9R,11R,15R)-9-chloro-11,15-dihydroxy-16,16-dimethyl-5,13-prostadienoic acid (active agent content: 3.5%) is triturated in portions with lactose, and polyvinylpyrrolidone 25,000 and cornstarch are admixed thereto. The mixture is granulated with aqua bidestillata, screened, and dried. Magnesium stearate is admixed, and the resultant press-molding composition is pressed into tablets having a diameter of 6 mm on a suitable tabletting press.

Composition of a tablet:

| | |
|---|---|
| β-Cyclodextrin clathrate (see above) | 2.86 mg |
| Lactose | 50.44 mg |
| Cornstarch | 24.00 mg |
| Polyvinylpyrrolidone 25,000 | 2.40 mg |
| Magnesium stearate | 0.30 mg |
| | 80.00 mg |

Tablets of 80 mg each are obtained, containing 100 μg of (5Z,13E)-(9R,11R,15R)-9-chloro-11,15-dihydroxy-16,16-dimethyl-5,13-prostadienoic acid.

EXAMPLE 4

The β-cyclodextrin clathrate of (5Z,13E)-(9R,11R,15R)-9-chloro-11,15-dihydroxy-16,16-dimethyl-5,13-prostadienoic acid (active agent content: 5.2%) is dissolved together with lactose in aqua bidestillata, dispensed by way of a suitable filter into a multivial, and frozen at −20° C. Subsequently the product is freeze-dried under vacuum for 24 hours.

Composition of a unit:

| | |
|---|---|
| β-Cyclodextrin clathrate (see above) | 1.94 mg |
| Lactose | 10.00 mg |
| Aqua bidest. | ad 2,000.00 mg |

In this way, formulations are obtained containing 100 μg of (5Z,13E)-(9R,11R,15R)-9-chloro-11,15-dihydroxy-16,16-dimethyl-5,13-prostadienoic acid per multivial.

We claim:

1. A pharmaceutical preparation comprising as the active component a β-cyclodextrin clathrate of a prostaglandin of the formula

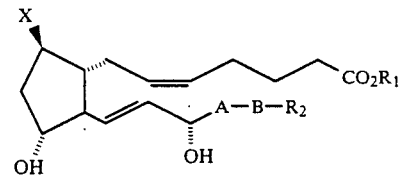

wherein
$R_1$ is hydrogen or alkyl of up to 10 carbon atoms,
$R_2$ is alkyl, cycloalkyl, or optionally substituted phenyl,
A and B jointly mean a direct bond or
A means alkylene of up to 10 carbon atoms and
B means an oxygen atom, a direct bond, or a —C≡C—bond, and
X means a chlorine or fluorine atom,
and a pharmaceutically acceptable excipient.

2. Preparation according to claim 1, containing a (5Z,13E)-(9R,11R,15R)-9-chloro-11,15-dihydroxy-16,16-dimethyl-5,13-prostadienoic acid β-cyclodextrin clathrate.

3. Preparation according to claim 1, containing a (5Z,13E)-(9R,11R,15R)-9-fluoro-11,15-dihydroxy-16-phenoxy-17,18,19,20-tetranor-5,13-prostadienoic acid-β-cyclodextrin clathrate.

4. Preparation according to claim 1, containing a (5Z,13E)-(9R,11R,15R)-9-chloro-11,15-dihydroxy-16-phenoxy-17,18,19,20-tetranor-5,13-prostadienoic acid-β-cyclodextrin clathrate.

5. Preparation according to claim 1, containing a (5Z,13E)-(9R,11R,15R)-9-fluoro-11,15-dihydroxy-16,16-dimethyl-5,13-prostadienoic acid-β-cyclodextrin clathrate.

6. Preparation according to claim 1, containing a (5Z,13E)-(9R,11R,15R)-9-chloro-11,15-dihydroxy-16,16,20-trimethyl-18,18,19,19-tetradehydro-5,13-prostadienoic acid-β-cyclodextrin clathrate.

7. Preparation according to claim 1, wherein the molar ratio of cyclodextrin/prostaglandin is 1 to 25:1.

8. Preparation according to claim 1, wherein said molar ratio is 3 to 15:1.

9. In a method of treating a patient in need of such treatment an effective amount of a prostaglandin, the improvement wherein the prostaglandin is administered in the form of a preparation of claim 1.

* * * * *